United States Patent
Strohl et al.

(10) Patent No.: US 9,637,549 B2
(45) Date of Patent: May 2, 2017

(54) ANTIBODY FC MUTANTS WITH ABLATED EFFECTOR FUNCTIONS

(71) Applicant: Janssen Biotech, Inc., Horsham, PA (US)

(72) Inventors: William Strohl, Spring House, PA (US); Omid Vafa, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/597,690

(22) Filed: Jan. 15, 2015

(65) Prior Publication Data

US 2015/0118227 A1 Apr. 30, 2015

Related U.S. Application Data

(62) Division of application No. 12/955,240, filed on Nov. 29, 2010, now Pat. No. 8,961,967.

(60) Provisional application No. 61/265,079, filed on Nov. 30, 2009.

(51) Int. Cl.
| | | |
|---|---|---|
| *C07K 16/32* | (2006.01) | |
| *C07K 16/00* | (2006.01) | |
| *C07K 16/28* | (2006.01) | |
| *A61K 38/00* | (2006.01) | |
| *A61K 39/00* | (2006.01) | |

(52) U.S. Cl.
CPC ............. *C07K 16/32* (2013.01); *C07K 16/00* (2013.01); *C07K 16/2887* (2013.01); *A61K 38/00* (2013.01); *A61K 2039/505* (2013.01); *C07K 2317/52* (2013.01); *C07K 2317/524* (2013.01); *C07K 2317/54* (2013.01); *C07K 2317/71* (2013.01); *C07K 2317/73* (2013.01); *C07K 2317/732* (2013.01); *C07K 2317/734* (2013.01)

(58) Field of Classification Search
CPC ........................ C07K 2317/71; C07K 2317/52
USPC ..................................... 424/133.1; 530/387.3
See application file for complete search history.

(56) References Cited

U.S. PATENT DOCUMENTS

| | | | |
|---|---|---|---|
| 5,624,821 A | 4/1997 | Winter et al. | |
| 5,834,597 A | 11/1998 | Tso et al. | |
| 7,597,889 B1 | 10/2009 | Armour et al. | |
| 8,961,967 B2 | 2/2015 | Strohl et al. | |
| 9,090,694 B2 | 7/2015 | Duffy et al. | |
| 9,212,227 B2 | 12/2015 | Duffy et al. | |
| 2007/0009523 A1 | 1/2007 | Presta | |
| 2007/0036799 A1 | 2/2007 | Stavenhagen et al. | |
| 2007/0148167 A1 | 6/2007 | Strohl | |
| 2011/0054151 A1 | 3/2011 | Lazar et al. | |
| 2011/0287032 A1 | 11/2011 | Lazar et al. | |
| 2013/0089550 A1 | 4/2013 | Lazar et al. | |
| 2014/0112924 A1 | 4/2014 | Lazar et al. | |
| 2014/0323315 A1 | 10/2014 | Bobrowicz et al. | |
| 2014/0377269 A1 | 12/2014 | Mabry et al. | |
| 2015/0337053 A1* | 11/2015 | McCarthy .......... | C07K 16/2887 424/133.1 |
| 2016/0077105 A1 | 3/2016 | Bobrowicz et al. | |
| 2016/0145350 A1 | 5/2016 | Lonberg et al. | |
| 2016/0176963 A1 | 6/2016 | Maurer et al. | |
| 2016/0264643 A1 | 9/2016 | Lazar et al. | |

FOREIGN PATENT DOCUMENTS

| | | |
|---|---|---|
| WO | WO 97/11971 A1 | 4/1997 |
| WO | WO 2005/040217 A2 | 5/2005 |
| WO | WO 2006/019447 A1 | 2/2006 |
| WO | WO 2006/055178 A3 | 5/2006 |
| WO | WO 2009/052439 A2 | 4/2009 |
| WO | WO 2009/100309 A2 | 4/2009 |

OTHER PUBLICATIONS

Vafa et al. (Methods 65:114-126 (2014)).*
PCT International Search Report dated Feb. 10, 2011.
Alegre, et al., "Effect of a single amino acid mutation on the activating and immunosuppressive properties of a "humanized" OKT3 monoclonal antibody," The Journal of Immunology, 148: 3461-3468 (1992).
Alegre, et al., "A Non-Activating "Humanized" Anti-CD3 Monoclonal Antibody Retains Immunosuppressive Properties in Vivo," Transplantation, 57: 1537-1543 (1994).
An, et al., "IgG2m4, an engineered antibody isotype with reduced Fc function," Landes Bioscience, 1(6): 1-8 (2009).
Armour, et al., "Recombinant human IgG molecules lacking Fc gamma receptor Receptor I binding and monocyte triggering activities," European Journal of Immunology, 29(8): 2613-2624 (1999).
Armour, et al., "Differential binding to human Fc gamma RIIa and Fc gamma RIIb receptors by human IgG wildtype and mutant antibodies," Molecular Immunology, 40: 585-593 (2003).
Boder, et al., "Yeast surface display for screening combinatorial polypeptide libraries," Nature Biotechnology, 15: 553-557 (1997).
Brekke, et al., "Human IgG isotype-specific amino acid residues affecting complement-mediated cell lysis and phagocytosis," European Journal of Immunology, 24: 2542-2547 (1994).
Brezski, et al., "Human Anti-IgG1 Hinge Autoantibodies Reconstitute the Effector Functions of Proteolytically Inactivated IgGs," The Journal of Immunology, 181: 3183-3192 (2008).
Brüggemann, et al., "Comparison of the Effector Functions of Human Immunoglobulins Using a Matched Set of Chimeric Antibodies," Journal of Experimental Medicine, 166: 1351-1261 (1987).
Canfield, et al., "The Binding Affinity of Human IgG for its High Affinity Fc Receptor is Determined by Multiple Amino Acids in the $C_H2$ Domain and is Modulated by the Hinge Region," Journal of Experimental Medicine, 173: 1483-1491 (1991).
Chappel, et al., "Identification of the $Fc_\gamma$ receptor class I binding site in human IgG through the use of recombinant IgG1/IgG2 hybrid and point-mutated antibodies," Proceedings of the National Academy of Science USA, 88: 9036-9040 (1991).
Chen, et al., "Cell-Surface Display of Heterologous Proteins: From High-Throughput Screening to Environmental Applications," Biotechnology and Bioengineering, 79: 496-503 (2002).

(Continued)

*Primary Examiner* — Lynn Bristol
(74) *Attorney, Agent, or Firm* — Eric Dichter

(57) ABSTRACT

Antibody and other Fc-containing molecules with variations in the Fc region reduce binding to Fc gamma receptors and resulting activity and can be used in the treatment of various diseases and disorders.

1 Claim, 13 Drawing Sheets

(56) References Cited

OTHER PUBLICATIONS

Clynes, et al., "Fc receptors are required in passive and active immunity to melanoma," Proceedings of the National Academy of Science USA, 95: 652-656 (1998).
Dorai, et al., "Aglycosylated Chimeric Mouse/Human IgG1 Antibody Retains Some Effector Function," Hybridoma, 10(2): 211-217 (1991).
Duncan, et al., "Localization of the binding site for the human high-affinity Fc receptor on IgG," Nature, 332: 563-564 (1988).
Herold, et al., "Anti-CD3 Monoclonal Antibody in New-Onset Type 1 Diabetes Mellitus," The New England Journal of Medicine, 346: 1692-1698 (2002).
Hoogenboom, et al., "Natural and designer binding sites made by phage display technology," Immunology Today, 21(8): 371-378 (2000).
Idusogie, et al., "Mapping of the C1q Binding Site on Rituxan, a Chimeric Antibody with a Human IgG1 Fc," Journal of Immunology, 164: 4178-4184 (2000).
Kretzschmar, et al., "Antibody discovery: phage display," Current Opinion in Biotechnology, 13: 598-602 (2002).
Labrijn, et al., "When binding is enough: nonactivating antibody formats," Current Opinion in Immunology, 20: 479-485 (2008).
Lazar, et al., "Engineered antibody Fc variants with enhanced effector function," Proceedings of the National Academy of Science USA, 103(11): 4005-4010 (2006).
Mattheakis, et al., "An in vitro polysome display system for identifying ligands from very large peptide libraries," Proceedings of the National Academy of Science USA, 91: 9022-9026 (1994).
Myszka, et al., "Improving biosensor analysis," Journal of Molecular Recognition, 12(5): 279-284 (1999).
Mueller, et al., "Humanized Porcine VCam-Specific Monoclonal Antibodies with Chimeric IgG2/G4 Constant regions Block Human Leukocyte Binding to Procine Endothelial Cells," Molecular Immunology, 34(6): 441-452 (1997).
Patel, et al., "An improved assay for antibody dependent cellular cytotoxicity based on time resolved fluorometry," Journal of Immunological Methods, 184: 29-38 (1995).

Sensel, et al., "Amino Acid Differences in the N-Terminus of $C_H2$ Influence the Relative Abilities of IgG2 and IgG3 to Activate Complement," Molecular Immunology, 34(14): 1019-1029 (1997).
Shields, et al., "High resolution mapping of the binding site on human IgG1 for Fc gamma RI, Fc gamma RII, Fc gamma RIII and FcRn and design of IgG1 variants with improved binding to the Fc gamma R," Journal of Biological Chemistry, 276(9): 6591-6604 (2001).
George P. Smith, "Filamentous Fusion Phage: Novel Expression Vectors that Display Cloned Antigens on the Virion Surface," Science, 228: 1315-1317 (1985).
Tao, et al., "Studies of aglycosylated Chimeric mouse-human IgG. Role of carbohydrate in the structure and effector functions mediated by the human IgG constant region," Journal of Immunology, 143(8): 2595-2601 (1989).
Wilkinson, et al., "Antibody-dependent cell-mediated cytotoxicity: a flow cytometry-based assay using fluorophores," Journal of Immunological Methods, 258: 182-191 (2001).
Wisecarver, et al., "A method for determination of antibody-dependent cellular cytotoxicity (ADCC) of human peripheral mononuclear cells," Journal of Immunological Methods, 79(2): 277-282 (1985).
Xu, et al., "In Vitro Characterization of Five Humanized OKT3 Effector Function Variant Antibodies," Cellular Immunology, 200, 16-26 (2000).
Zhiqiang An, et al., "IgG2m4, an engineered antibody isotype with reduced Fc function," mAbs, Landes Bioscience, 1(6): 572-579 (2009).
Seth, et al., "T. 124. Mutation P331S in the Fc Domain of an Anti-CD20 SMIP™ Protein Confers Impaired in vivo B Cell Depletion Activity in Lymphoid Tissues of Cynomolgus Monkeys," Clinical Immunology, 131: S88 (2009).
Strohl, et al., "Optimization of Fc-mediated effector functions of monoclonal antibodies," Current Opinions in Biotechnology, 20: 685-691 (2009).
Kinder, et al., "An Fc engineering approach that modulates antibody-dependent cytokine release without altering cell-killing functions," mAbs, 7(3): 494-504 (2015).
Jochen G. Salfeld, et al., "Isotype selection in antibody engineering," Nature Biotechnology, 25(12): 1369-1372 (2007).

* cited by examiner

*Fig. 1*

```
          218                                               267
hIgG2  KCC---VECPPCPAPPVA-GPSVFLFPPKPKDTLMISRTPEVTCVVVDVS
hIgG4  KYG---PPCPSCPAPEFLGGPSVFLFPPKPKDTLMISRTPEVTCVVVDVS
hIgG1  KSCDKTHTCPPCPAPELLGGPSVFLFPPKPKDTLMISRTPEVTCVVVDVS
        *    ** ****    **************************

268                                               317
hIgG2  HEDPEVQFNWYVDGVEVHNAKTKPREEQFNSTFRVVSVLTVVHQDWLNGK
hIgG4  QEDPEVQFNWYVDGVEVHNAKTKPREEQFNSTYRVVSVLTVLHQDWLNGK
hIgG1  HEDPEVKFNWYVDGVEVHNAKTKPREEQYNSTYRVVSVLTVLHQDWLNGK
        **** ********************  *** ******* *******

318                                               367
hIgG2  EYKCKVSNKGLPAPIEKTISKTKGQPREPQVYTLPPSREEMTKNQVSLTC
hIgG4  EYKCKVSNKGLPSSIEKTISKAKGQPREPQVYTLPPSQEEMTKNQVSLTC
hIgG1  EYKCKVSNKALPAPIEKTISKAKGQPREPQVYTLPPSRDELTKNQVSLTC
       ********* **  ******* ****************   ********

368                                               417
hIgG2  LVKGFYPSDIAVEWESNGQPENNYKTTPPMLDSDGSFFLYSKLTVDKSRW
hIgG4  LVKGFYPSDIAVEWESNGQPENNYKTTPPVLDSDGSFFLYSRLTVDKSRW
hIgG1  LVKGFYPSDIAVEWESNGQPENNYKTTPPVLDSDGSFFLYSKLTVDKSRW
       ****************************  ********** ********

418                447
hIgG2  QQGNVFSCSVMHEALHNHYTQKSLSLSPGK
hIgG4  QEGNVFSCSVMHEALHNHYTQKSLSLSLGK
hIgG1  QQGNVFSCSVMHEALHNHYTQKSLSLSPGK
       * *************************** **
```

ANTIBODY FC MUTANTS WITH ABLATED EFFECTOR FUNCTIONS

CROSS-REFERENCE TO RELATED APPLICATIONS

This application is a divisional of U.S. application Ser. No. 12/955,240, filed 29 Nov. 2010, now U.S. Pat. No. 8,961,967, granted 24 Feb. 2015, which claims the benefit of U.S. Provisional Application Ser. No. 61/265,079, filed 30 Nov. 2009, the entire contents of which are incorporated hereby by reference in their entireties.

BACKGROUND

Field of the Invention

The invention relates to human antibody IgG2 constant regions (Fc regions) mutated such that they substantially lose the capacity to specifically bind Fcγ receptors or activate mitogenic responses by immune cells by Fc receptor mediated cross-linking of surface target antigens. The invention also provides novel antibodies into which the mutated IgG2 constant regions can be incorporated.

Discussion of the Field

Antibodies that target cell surface antigens trigger unwanted immunostimulatory and effector functions associated with Fc receptor (FcR) engagement on immune cells and the activation of complement. As therapeutic antibodies and Fc-fusion constructs intended to target and activate or neutralize target ligand functions but not damage or destroy local cells or tissues that are needed, Fc mutants with ablated effector functions have been sought.

Human IgG isotypes (the subclasses of mature gamma globulin class G antibodies; IgG1, IgG2, IgG3 and IgG4) exhibit differential capacity to recruit immune functions, such as antibody-dependent cellular cytotoxicity (ADCC, e.g., IgG1 and IgG3), antibody-dependent cellular phagocytosis (ADCP, e.g., IgG1, IgG2, IgG3 and IgG4), and complement dependent cytotoxicity (CDC, e.g., IgG1, IgG3). Isotype-specific engagement of such immune functions is based on selectivity for Fc receptors on distinct immune cells and the ability to bind C1q and activate the assembly of a membrane attack complex (MAC). Among the various isotypes, relative affinity for Fcγ receptors (e.g., FcγRI, FcγRIIa/b/c, FcγRIIIa/b) is high for IgG1 and IgG3, however, there is minimal affinity for IgG2 (restricted to the FcγRIIa 131H polymorphism), and IgG4 only has measurable affinity for FcγRI. Using comparative sequence analysis and co-crystal structures, the key contact residues for receptor binding have been mapped to the amino acid residues spanning the lower hinge and CH2 region. Using standard protein engineering techniques, some success in enhancing or reducing the affinity of an antibody preparation for Fc receptors and the C1q component of complement has been achieved.

Among the isotypes, IgG2 is least capable of binding the family of Fc receptors. Using IgG2 as the starting point, efforts have been made to find a mutagen with diminished effector functions but which retains FcRn binding, prolonged stability, and low immunogenicity. Improved mutants of this nature may provide improved antibody therapeutics with retained safety.

SUMMARY OF THE INVENTION

The present invention provides the compositions of modified, glycosylated immunoglobulin constant domains useful in engineering of antibody or antibody-like therapeutics, such as those comprising an Fc region, and targeting cell surface ligands. The composition of the invention is an IgG2 Fc mutant exhibiting diminished FcγR binding capacity but having conserved FcRn binding. These IgG Fc mutants enable therapeutic targeting of soluble or cell surface antigens while minimizing Fc-associated engagement of immune effector function and complement mediated cytotoxicity. In one aspect, the IgG2 Fc mutant comprises V234A, G237A, P238S according to the EU numbering system. In another aspect, the IgG2 Fc mutant comprises V234A, G237A, H268Q or H268A, V309L, A330S, P331S according to the EU numbering system. In a particular aspect, the the IgG2 Fc mutant comprises V234A, G237A, P238S, H268A, V309L, A330S, P331S, and, optionally, P233S according to the EU numbering system.

In one embodiment, the IgG2 Fc mutant compositions are used in indications where retention of therapeutic antibody (or Fc-fusion) half-life is conserved through interactions with FcRn, while potential toxicity derived from activation of FcγRs associated with immune and effector functions such as i) antibody dependent cytotoxicity (ADCC), ii) complement dependent cytotoxicity (CDC), iii) antibody dependent cellular phagocytosis (ADCP), iv) FcR-mediated cellular activation (e.g. cytokine release through FcR cross-linking), and v) FcR-mediated platelet activation/depletion is minimized or eliminated. In one aspect, the IgG2 Fc mutations are incorporated into therapeutic antibodies or Fc-fusions of binders, such as multivalent binders, targeting ligands on cells involved in neurological disorders, such as basal cell ganglion; immune system disorders such as those related to B-cell or T-cell activation, or to cells involved in tissue repair or healing, such as fibroblasts or stem cells.

In another embodiment, the IgG2 Fc mutant comprises a pharmaceutical composition. In another embodiment the IgG2 Fc mutant comprises a portion of a pharmaceutically active molecule. The pharmaceutical compositions comprising the IgG2 Fc mutant or active IgG2 Fc mutant-comprising molecules are useful for the treatment of diseases characterized by the migration and concentration of macrophages or monocytes. In one aspect, the IgG2 Fc mutant-comprising molecules are useful for binding a target within a neurological tissue, an endocrine tissue, a vascular tissue, a cardiac tissue, a synovial tissue, a dermal tissue, or a mucosal tissue. One of the many uses of the IgG2 Fc mutants of the invention is in the treatment of Graft-v.-host disease; host-v.-graft disease; organ transplant rejection; bone-marrow transplant rejection; autoimmunity such as vasculitis, autoimmune haemolytic anaemia, autoimmune thrombocytopenia and arthritis; alloimmunity, such as fetal/neonatal alloimmune thrombocytopenia; asthma and allergy; chronic or acute inflammatory diseases such as Crohn's Disease or scleroderma; Alzheimer's Disease, coronary artery occlusion.

BRIEF DESCRIPTION OF THE DRAWING

FIG. 1 shows an alignment of the amino acid sequences of wild type human IgG2 (SEQ ID NO: 1), IgG4 (SEQ ID NO: 2), and IgG1 (SEQ ID NO: 3) showing the corresponding EU numbering for each residue; the hinge region of the IgG2 begins at EU residue 218.

BRIEF DESCRIPTION OF THE SEQUENCE LISTING

Figure 2:
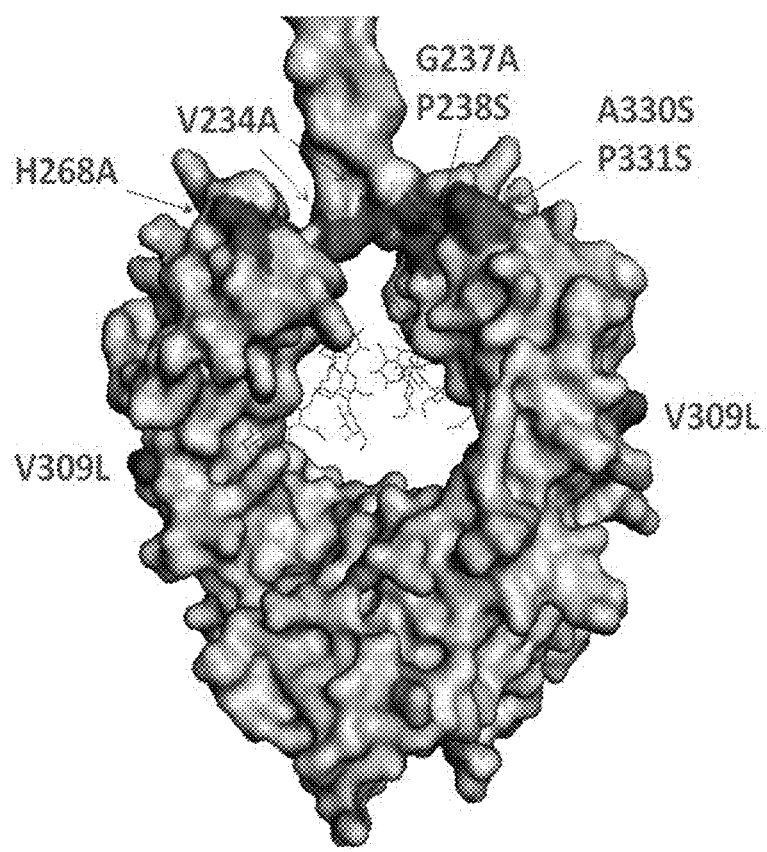
FIG. 2 shows the structure of an Fc fragment showing the surface positions of the residues modified (EU numbering).

| SEQ ID NO: | Description | Features |
|---|---|---|
| 1 | IgG2-Fc; Human Ig gamma class, subclass 2 hinge, CH2 and CH3 domains | Residue 1 corresponds to EU 218, residues 13-17 may be PVAGP (wt), PAAAP, PAAAS, and SAAAS; Residue 47 may be May be H (wt), Q, or A; residue 109-110 may be AP (wt) or SS. |
| 2 | IgG4-Fc; Human Ig gamma class, subclass 4, hinge, CH2 and CH3 domains | Residue 1 corresponds to EU 218 |
| 3 | IgG1-Fc; Human Ig gamma class, subclass, hinge, CH2 and CH3 domains | Residue 1 corresponds to EU 218 |
| 4 | PAAAP | mutated IgG constant region residues 233, 234, 235, 237, and 238 |
| 5 | PAAAS | mutated IgG constant region residues 233, 234, 235, 237, and 238 |
| 6 | SAAAS | mutated IgG constant region residues 233, 234, 235, 237, and 238 |

DETAILED DESCRIPTION OF THE INVENTION

Abbreviations

ADCC=antibody-dependent cellular cytotoxicity; ADCP, antibody-dependent cellular phagocytosis; CDC=complement-dependent cytotoxicity; IgG=immunoglobulin G; ITAM=immunoreceptor tyrosine activating motif; ITIM=immunoreceptor tyrosine inhibitory motif; Mab=monoclonal antibody; FDCR=Fc-dependent cytokine release; FcγR, FcgR, or FcgammaR=Fc gamma receptor Definitions & Explanation of Terminology "Antibody-dependent cell-mediated cytotoxicity" or ADCC" refers to a form of cytotoxicity in which secreted Ig bound onto Fc receptors (FcRs) present on certain cytotoxic cells (e.g., Natural Killer (NK) cells, neutrophils, and macrophages) that enables these cytotoxic effector cells to bind specifically to an antigen-bearing target cell and subsequently kill the target cell with cytotoxins. Ligand specific high-affinity IgG antibodies directed to the surface of target cells stimulate the cytotoxic cells and are absolutely required for such killing. Lysis of the target cell is extracellular, requires direct cell-to-cell contact, and does not involve complement.

The ability of any particular antibody to mediate lysis of the target cell by ADCC can be assayed. To assess ADCC activity, an antibody of interest is added to target cells displaying the target ligand in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al, 1985, 19:211; Bruggemann et al, 1987, J Exp Med 166: 1351; Wilkinson et al, 2001, J Immunol Methods 258:183; Patel et al, 1995 J Immunol Methods 184:29 (each of which is incorporated by reference). Alternatively, or additionally, ADCC activity of the antibody of interest may be assessed in vivo, e.g., in an animal model, such as that disclosed in Clynes et al, 1998, PNAS USA 95:652, the contents of which are incorporated by reference in its entirety.

"Complement-directed cytotoxicity" or CDC refers to the form of cytotoxicity in which the complement cascade is activated by the complement component C1q binding to antibody Fc.

The terms "Fc," "Fc-containing protein" or "Fc-containing molecule" as used herein refer to a monomeric, dimeric or heterodimeric protein having at least an immunoglobulin CH2 and CH3 domain. The CH2 and CH3 domains can form at least a part of the dimeric region of the protein/molecule (e.g., antibody).

The term "monoclonal antibody" as used herein is a specific form of Fc-containing protein comprising at least one ligand binding domain which retains substantial homology to at least one of a heavy or light chain antibody variable domain of at least one species of animal antibody.

"Wild type human IgG2 Fc region" refers to a human IgG Fc region that comprises the amino acid sequence of SEQ ID NO: 1 or a fragment thereof, which is from residue K218 to residue K447 of the human IgG heavy chain, according to the EU numbering of Kabat Amino acids in the constant region are numbered by alignment with the human IgG1 antibody, EU IgG1 (SEQ ID NO: 3) (see Cunningham et al., 1970 J. Biol. Chem., 9: 3161-70). That is, the heavy and light chains of an antibody are aligned with the heavy and light chains of EU to maximize amino acid sequence identity and each amino acid in the antibody is assigned the same number as the corresponding amino acid in EU. The EU numbering system is conventionally used in the art (see generally, Kabat et al, Sequences of Protein of Immunological Interest, NIH Publication No. 91-3242, US Department of Health and Human Services (1991)). According to this convention, the "wildtype IgG2" constant region described lacks an amino acid at position 236 (FIG. 1, SEQ ID NO: 1).

Overview

The present invention was motivated by an interest in identifying an Fc domain for use in the manufacture of therapeutic antibodies, Fc-fusions, and like biopharmaceuticals with improved safety in terms of the inability to cause cytokine release or damage or kill target ligand displaying cells and tissues surrounding targeted cells.

Human IgG4 isotype antibodies and Fc-fusion proteins do not elicit significant ADCC (by NKs, expressing exclusively FcgRIIIa), but do retain the ability to induce phagocytosis (ADCP) by macrophages (expressing FcγRI, IIa and IIIa) and possibly activate monocytes when in an immune complex and attributable to the distribution of activating FcγRs on specific immune cells. Efforts to minimize the residual activity resulted in a development of and use of mutant comprising V234A, L235A (ala/ala) in the wildtype IgG4 Fc (SEQ ID NO: 2).

Armour et al generated multiple point mutations in IgG2 to minimize binding to FcgRI (Armour et al, 1999) and FcgRIIa and Ma (Armour et al. 2003). Additional mutations disclosed in Mueller et al.'s patent application (PCTWO97/11971) are derived from hybrids of IgG2/IgG4, consisting of an IgG2 CH2 and an IgG4 CH3 domain, specifically residues 330 and 331 are from IgG4 in the IgG2 mutants of the present invention. Muting or silencing efforts to diminish immunostimulatory effects have also used. IgG2 or IgG4 or domain swapping among the two subclasses to generate mAbs with minimal effector function in IgG1 (SEQ ID NO: 3) (Tao et al, 1991). The patent application of Strohl (US2007/0148167) discloses four mutations in IgG2 at residues EU positions 268, 309, 330 and 331. Shields et al. (2001) discloses an additional substitution, H268A.

The present invention is a demonstration for the first time of substitutions in multiple positions of the IgG2 constant regions (Fc) with IgG4 residues H268Q or A, V309L, A330S and P331S according to Kabat/EU numbering system. The directed selection of multiple residue substitutions unexpectedly provided a functional Fc domain for use in antibody engineering and used as a fusion polypeptide as well as the possibility of providing a therapeutic entity which is devoid of measurable effector function.

The multi-substituted IgG2 mutants were selected on the bases of their relative affinities for human FcRs (FcγRI, FcγRIIa, FcγRIIb, FcγRIIIa and FcRn) assessed by Alpha Screen competition assays and SPR/Biacore analyses. These mutants were further tested and ranked in the appropriate cellular systems for their ability to induce CDC, ADCC and ADCP as well as trigger TNF-α secretion by PBMCs. In the set of experimental data provided herein, the IgG2 mutants were compared to known preparations or mutants including; IgG1 ag and IgG4 Ala/Ala in addition to wildtype IgG1 and IgG2. Further analyses of these mutants in several in vitro bioassays demonstrated that minimal to undetectable levels of activity and greatly ablated binding affinity for FcRs. Based on these screens, an IgG2 Fc mutant, designated as IgG2c4d, has been identified that has no detectable affinity or avidity for FcRs (monomeric v. bi-multimeric ligand binding) and is devoid of activity in the various aforementioned effector/immunostimulatory bioassays. The IgG2c4d Fc comprises the alanine, serine, and leucine substitutions: V234A, G237A, P238S, H28A, V309L, A330S, P331S (EU numbering). The seven residue substituted IgG2, IgG2c4d, may be considered the first truly "silenced" Fc in its inability to bind FcRs, mediate effector functions, or engage Fc-mediated cytokine release.

Based on the present discovery, subsets of the seven mutations of IgG2c4d can be used, or combined with other amino acid mutants, or the mutations can be used in another IgG isotype to achieve similar or selective silencing of effector functions as taught herein and combined with what is known in the art.

As specifically exemplified herein, the triplet V234A, G237A, P238S substitutions reduce FcγRIIa binding affinity and FcγRIIa binding avidity and ablate ADCP and Fc-dependent cytokine release while maintaining the FcRn binding affinity of the molecule.

TABLE 1

Summary of Biacore relative binding affinity.

| Isotype/Variant | FcγRI | FcγRIIa | FcγRIIIa |
|---|---|---|---|
| IgG1 | +++++ | +++ | +++ |
| IgG1 agly (N297A) | +++ | − | +/− |
| IgG4 S > P, ala/ala | +++ | − | +/− |
| IgG2 | − | +++ | +/− |
| IgG2m4 | − | +++ | +/− |
| IgG2c4a | − | +++ | +/− |
| IgG2c4b | + | − | +/− |
| IgG2c4d | − | − | − |
| IgG2c4e | − | − | − |

TABLE 2

Summary of relative avidity.

| Isotype/Variant | FcγRI avidity | FcγRIIa avidity | FcγRIIIa avidity |
|---|---|---|---|
| IgG1 | +++++ | ++++ | +++ |
| IgG1 agly (N297A) | +++ | − | − |
| IgG4 S > P, ala/ala | +++ | ++ | − |
| IgG2 | − | +++ | − |
| IgG2m4 | − | +++ | − |
| IgG2c4d | − | − | − |

TABLE 3

Summary of effector functions and cytokine release (CR).

| Isotype/Variant | ADCC | ADCP | CDC | Cytokine Release |
|---|---|---|---|---|
| IgG1 | +++++ | +++++ | +++++ | +++++ |
| IgG1 agly (N297A) | − | +++ | − | ++ |
| IgG4 S > P, ala/ala | − | ++ | − | ++ |
| IgG2 | − | ++ | − | +++ |
| IgG2m4 | − | ++ | − | ++ |
| IgG2c4d | − | − | − | − |

Method of Making the Altered Fc-Containing Molecules

The sites for substitution were chosen based on the desire produce a composition having the structural features of a native antibody Fc, retained FcRn binding, good stability, and a diminished capacity to stimulate the complement cascade, cell lysis, cell phagocytosis or cytokine release.

As IgG class antibodies are bivalent, having two complete Fv domains consisting of the heavy and light variable domains in functional association. Bivalency provides avidity effects as well as the ability to cross-link target antigen or Fc receptors on the same or distinct cells, thereby provoking a spectrum of the non-target specific receptor binding driven bioactivities of antibodies. For this reason, the Fc mutants of the present invention were tested within an "avidity context" meaning that the Fc mutants of IgGs were multimerized on a surface and tested for interaction with a multimer of specific Fc receptors.

Biological Characterization of the Mutants

Fc-containing proteins can be compared for functionality by several well-known in vitro assays. In particular, affinity for members of the FcγRI, FcγRII, and FcγRIII family of Fcγ receptors is of interest. These measurements can be made using recombinant soluble forms of the receptors or cell-associated forms of the receptors. In addition, affinity for FcRn, the receptor responsible for the prolonged circulating half-life of IgGs, can be measured, for example, using a ligand bound bead format of "ALPHASCREEN" using recombinant soluble FcRn. ALPHASCREEN, used in high throughput screening, is a homogenous assay technology which allows detection of molecular events such as binding. Coated "Donor" and "Acceptor" beads are the basis of the assay technology. As a bead based assay, ALPHASCREEN works through the interaction of the beads in close proximity, resulting in a cascade of chemical reactions that act to produce a greatly amplified signal. Direct or indirect, e.g., competitive binding, measurements can be applied for assessing relative affinities and avidities among and between proteins.

The natural evolution of human IgG isotypes (e.g., IgG1, IgG2, IgG3 and IgG4), has allowed each to exhibit a different spectrum of capacities to recruit immune functions, such as antibody-dependent cellular cytotoxicity (ADCC, e.g., IgG1 and IgG3), antibody-dependent cellular phagocytosis (ADCP, e.g., IgG1, IgG2, IgG3 and IgG4), and complement dependent cytotoxicity (CDC, e.g., IgG1, IgG3). The isotype-specific engagement of these functions is based on differential selectivity for Fc receptors which resides on distinct immune cells, as well as the ability to bind C1q and activate the assembly of a membrane attack complex (MAC) resulting in CDC and CDP (complement dependent phagocytosis) through specific receptor binding complement components on effector macrophages. The hierarchy of ability to bind the initial component, C1q, of the complement cascade, of human isotypes is IgG1>IgG3>IgG2>IgG4 although complement activation by IgG2 and IgG4 in microbial infection is well-documented.

Cell-based functional assays, such as ADCC and CDC, provide insights into the likely functional consequences of particular variant structures. Antibody-dependent cell-mediated cytotoxicity (ADCC) is a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. In one embodiment, the ADCC assay is configured to have NK cells as the primary effector cell, reflecting the functional effects on the FcγRIIIA which is the only Fcγ-type receptor known to be expressed by these cells.

Phagocytosis assays may also be used to compare immune effector functions of different mutants, as can assays that measure cellular responses, such as superoxide or inflammatory mediator release. In vivo models have proved useful in the study of Fc variants. For example, as demonstrated using mutants of anti-CD3 antibodies to measure T cell activation in mice, an activity that is dependent on Fc domains engaging specific ligands, such as Fcγ receptors. Antibody directed activation of macrophages mediates antibody-dependent cellular phagocytosis (ADCP), causing opsonized target cells to be engulfed and digested by macrophages. In vitro, differentiated macrophages expressing high levels of FcRs can be differentiated into the M1 phenotype using IFNγ or GM-CSF to expressed elevated levels of all FcRs (FcγRI, FcγRIIa, FcγRIIIa) relative to monocytes. Such assays are known to those skilled in the art of antibody engineering.

Method of Making the Antibody

Routine recombinant processes were used to create directed mutations in the sequences for the human IgG2 constant domains used as the starting point in the generation and testing of Fc mutants. It will be appreciated to those skilled in the art that various techniques for creating changes in coding sequences can be used to create vectors suitable for the expression of the desired amino acid sequences in a variety of host cells for recovery and testing.

Host Cell Selection or Host Cell Engineering

As described herein, the host cell chosen for expression of the recombinant Fc-containing protein or monoclonal antibody is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein.

Further, the host cell may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof.

Alternatively, the host cell may be selected from a species or organism incapable of glycosylating polypeptides, e.g. a prokaryotic cell or organism, such as natural or engineered *E. coli* spp, *Klebsiella* spp., or *Pseudomonas* spp.

Antibodies

An antibody described in this application can include or be derived from any mammal, such as, but not limited to, a human, a mouse, a rabbit, a rat, a rodent, a primate, a goat, or any combination thereof and includes isolated human, primate, rodent, mammalian, chimeric, humanized and/or CDR-grafted antibodies, immunoglobulins, cleavage products and other specified portions and variants thereof.

The antibodies, Fc-comprising proteins, or Fc fragments described herein can be derived in several ways well known in the art. In one aspect, the antibodies are conveniently obtained from hybridomas prepared by immunizing a mouse or other animal with the target peptides, cells or tissues extracts. The antibodies can thus be obtained using any of the hybridoma techniques well known in the art, see, e.g., Harlow and Lane, antibodies, a Laboratory Manual, Cold Spring Harbor, N.Y. (1989) entirely incorporated herein by reference.

The antibodies or Fc-fusion proteins or components and domains thereof may also be obtained from selecting from libraries of such domains or components, e.g., a phage library. A phage library can be created by inserting a library of random oligonucleotides or a library of polynucleotides containing sequences of interest, such as from the B-cells of an immunized animal or human (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000, Immunol Today 21(8) 371-8). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody libraries also can be created synthetically by selecting one or more human framework sequences and introducing collections of CDR cassettes derived from human antibody repertoires or through designed variation (Kretzschmar and von Ruden 2000, Current Opinion in Biotechnology, 13:598-602). The positions of diversity are not limited to CDRs, but can also include the framework segments of the variable regions or may include other than antibody variable regions, such as peptides.

Other libraries of target binding components which may include other than antibody variable regions are ribosome display, yeast display, and bacterial displays. Ribosome display is a method of translating mRNAs into their cognate proteins while keeping the protein attached to the RNA. The nucleic acid coding sequence is recovered by RT-PCR (Mattheakis, L. C. et al. 1994. Proc. Natl. Acad. Sci. USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based on fusion of the target to exported bacterial proteins that associate with the cell membrane or cell wall (Chen and Georgiou 2002. Biotechnol Bioeng, 79:496-503).

In comparison to hybridoma technology, phage and other antibody display methods afford the opportunity to manipulate selection against the antigen target in vitro and without the limitation of the possibility of host effects on the antigen or vice versa.

The invention also provides for nucleic acids encoding the compositions of the invention as isolated polynucleotides or as portions of expression vectors including vectors compatible with prokaryotic, eukaryotic or filamentous phage expression, secretion and/or display of the compositions or directed mutagens thereof.

Use of the Fc-Containing Molecules

The compositions (antibody, Fc-fusions, Fc fragments) generated by any of the above described methods may be used to diagnose, treat, detect, or modulate human disease or specific pathologies in cells, tissues, organs, fluid, or, generally, a host. As taught herein, modification of the Fc portion of an antibody, Fc-fusion protein, or Fc fragment to reduce or ablate Fc gamma receptor binding and specified effector functions, but where the antibody retains the original targeting properties, provides antibodies and Fc-constructs with a superior spectrum of activities, biophysical properties, stability and ability to persist in the body of a host.

The diseases or pathologies that may be amenable to treatment using a composition provided by the invention include, but are not limited to: neurological disorders, such as but not limited to Alzheimer's disease and including neuropathic pain; dermatological disease; metabolic diseases; osteoarthritis; and conditions resulting from burns or injury; cardiovascular disorders including but not limited to myocardial infarction, congestive heart failure, stroke, ischemic stroke, and hemorrhage; as well as general immune mediated disorders, including the rheumatic diseases, psoriasis, and scleroderma.

While having described the invention in general terms, the embodiments of the invention will be further disclosed in the following examples that should not be construed as limiting the scope of the claims.

EXAMPLE 1

Construction of and Testing of Fc Mutants

A series of constructs with mutated derived from a human IgG2 antibody as shown in Table 4 were constructed using standard recombinant methods. For antibodies with complete variable domains, the known CDR sequences of anti-HER2 and anti-CD20 antibodies were used to construct isotype and Fc mutants as indicated. The antibody mutants were expressed transiently in 293T cells using standard cloning and expression procedures. MAbs were purified using protein A columns to greater than 95% homogeneity prior to further experimental analyses.

TABLE 4

| Subclass & designation | Mutations (EU Numbering) |
| --- | --- |
| IgG1 | |
| IgG1 Ag | N297A |
| IgG4 A/A | S228P, F234A, L235A |
| IgG2 | |
| IgG2m4 | H268Q, V309L, A330S, P331S |
| IgG2c4a | H268A, V309L, A330S, P331S |
| IgG2c4b | V234A, G237A, H268Q, V309L, A330S, P331S |
| IgG2c4c | V234A, G237A, H268A, V309L, A330S, P331S |
| IgG2c4d | V234A, G237A, P238S, H268A, V309L, A330S, P331S |
| IgG2c4e | P233S, V234A, G237A, P238S, H268A, V309L, A330S, P331S |

Biacore Studies of Affinities

Surface plasmon resonance experiments were performed using a Biacore 3000 optical biosensor (Biacore AB, Uppsala, Sweden; currently part of GE Healthcare). The experiments were performed at 25° C. in D-PBS buffer containing 3 mM EDTA and 0.01% surfactant P20. To analyze the interaction of the receptors with Fc mutants a capture surface was generated by covalent coupling of mouse anti-His IgG (R&D systems cat#MAB050) to a CM-5 sensor chip. The anti-His Ab was diluted into 10 mM sodium acetate buffer pH 4.5 (Biacore AB) and coupled to the carboxymethylated dextran surface of the CM-5 chip (~3000 RU) using the manufacturer instructions for amine-coupling chemistry. The remaining reactive groups on the surface were deactivated using ethanolamine-HCl. To perform kinetics experiments 165, 351 and 208 response units (RU) of FcγRI, FcγRII and FcγRIII, respectively were captured on this surface. Receptor capture was followed by injection of a serial dilution of wild type or Fc mutants (from 4000 nM to 3.9 nM in 4-fold dilution steps) at 30 uL/min. The association phase was monitored for 3 minutes. This was followed by buffer flow for 20 minutes to monitor binding dissociation. The capture surface was regenerated using a 9 seconds pulse of 100 mM phosphoric acid at 100 uL/min followed by injection of running buffer.

Double reference subtraction of the data was performed to correct for buffer contribution to the signal and instrument noise (Myszka 1999) using the Scrubber software version 1.1 g (BioLogic Software) for referencing. After this initial data processing, kinetic analysis of the data was performed using the BIA evaluation software, version 4.0.1 (Biacore, AB) assuming a simple 1:1 binding model.

AlphaScreen and Binding Studies

Both competition and direct binding of IgGs to various FcγRs was assessed using the homogeneous bead-based binding assay, AlphaScreen™ (PerkinElmer, Waltham, Mass.). In brief, experiments were carried out as previously described (Lazar et al 2006 Proc Natl Acad Sci USA 103(11): 4005-10) with minor modifications. FcγRI, IIa, were purchased from R&D systems. FcγRIIIa and FcRn were cloned, expressed and purified. IgG Fc mutants were tested in competition binding against biotinylated CNT06234 (a nonspecific control human IgG1 subclass antibody) or anti-Her2/neu (a human IgG2 antibody) which were biotinylated using NLS-biotin, Pierce, 2:1 ratio.

In competition binding studies, biotinylated antibodies were added to a final assay concentration of 200 ng/ml, followed by competing test antibodies at designated final concentrations specified in each experimental figure. FcγRs were added at 200 ng/ml final concentration to 96-well plates, followed by the serial addition of streptavidin donor and Ni-chelate acceptor beads. After sealing plates and shaking at room temperature, the plates were read using the Envision plate reader and data was graphed and plotted in GraphPad Prism. Avidity studies were carried out similar to the completion studies, with the exception that test IgG molecules were biotinylated at a 2:1 ratio and direct FcR binding was assessed in the absence of competition against a control antibody.

Results

The relative affinities of the IgG variants for human FcRs (FcγRI, FcγRIIa, FcγRIIb, and FcγRIIIa) assessed by SPR/Biacore analyses and derived from the sensograms are shown in Table 5.

TABLE 5

Biacore data for the interaction of Fc mutants with Fc receptors.

| Fc | Fcg RI $K_D$ (uM) | Fcg RIIa $K_D$ (uM) | Fcg RIIIa $K_D$ (uM) |
| --- | --- | --- | --- |
| huIgG1 | 0.013* | 1.7 | 0.16* |
| huIgG1-Ag | 3.7 | >170 | >95 |
| huIgG4 Ala-Ala, Ser-Pro | 15 | 150 | 55 |
| huIgG2 | 120 | 1 | 41 |
| huIgG2m4 | 210 | 2.7 | 95 |
| huIgG2c4a | 160 | 2.2 | 85 |
| huIgG2c4b | 38 | 170 | >95 |
| huIgG2c4c | 0.044* | 19 | 0.64* |
| huIgG2c4d | >210 | >170 | >95 |
| huIgG2c4e | >210 | >170 | >95 |

These numbers correspond to the parameters generated for the global fit of one experiment.

For these 4 sets of data the affinities were obtained by performing a fit using a simple 1:1 binding model kinetic fit. For all others, the affinities were obtained by performing a fit using a simple 1:1 binding steady state affinity analysis.

Figure 3A:
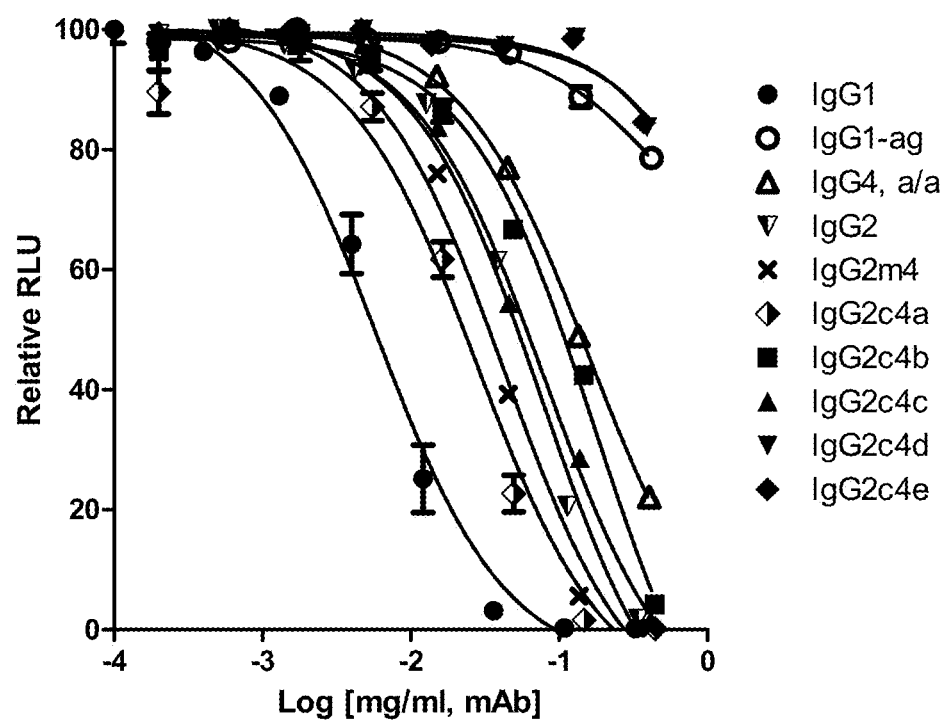
FIGS. 3A-C are graphs showing the competition of each isotype and mutant constructed as an anti-Her2/neu binding antibody with antibody of the human IgG1 wildtype isotype using the AlphaScreen bead assay platform: FcgRI (not shown), FcgRIIa (A), FcgRIIb (B), FcgRIIIa (not shown), and FcRn (C).
Figure 3B:
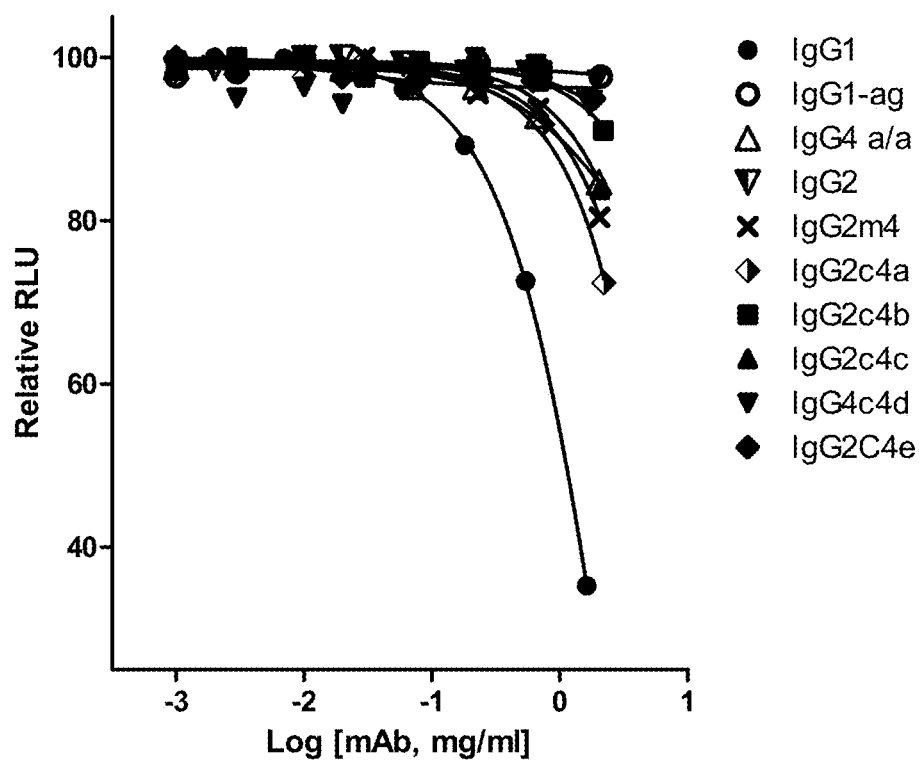
Figure 3C:
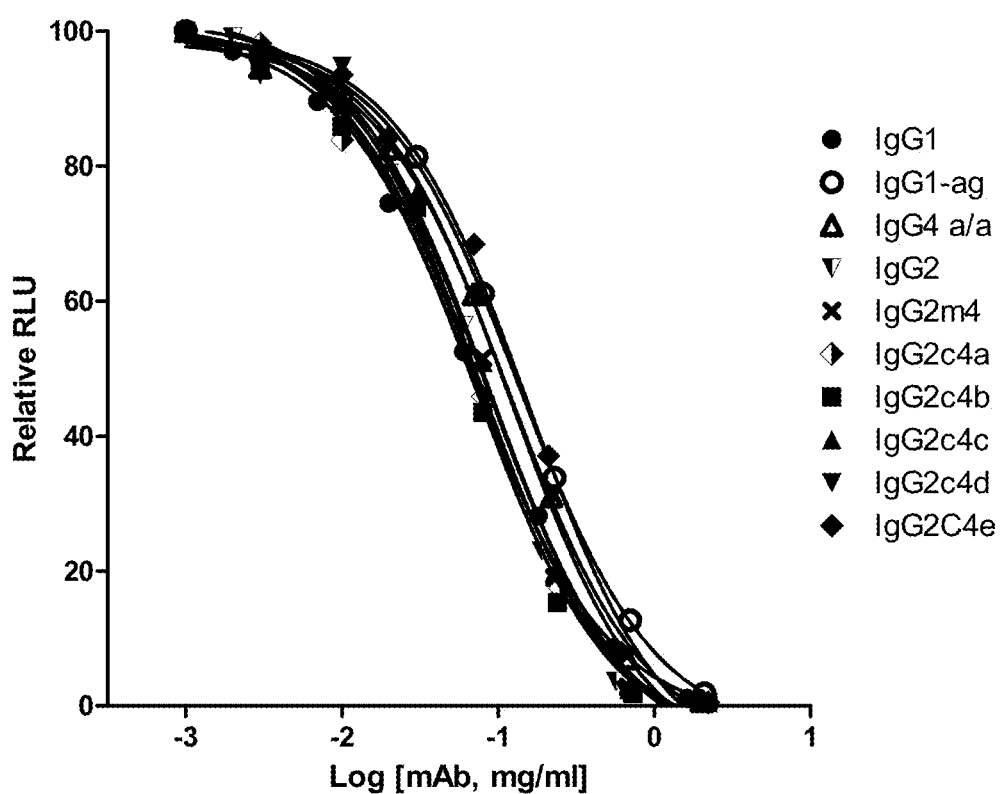

The relative affinities of the IgG mutants for human FcRs (FcγRIIa, FcγRIIb, and FcRn) in an avidity context, that is for bivalent antibody binding to a dense target field, measured using Alpha Screen™ competition assays with human IgG1 (CNTO6234) are shown in FIGS. 3A-C, respectively.

The experimental data demonstrated that IgG2 mutants as well as IgG1 ag and IgG4 Ala/Ala show significantly decreased binding affinity to Fc gamma receptors compared to IgG1, while retaining their capacity to bind to FcRn (the neonatal Fc receptor conferring in vivo half-life). Specifically, in competition binding against IgG2 and in binding to FcgRIIa ranking from high to lowest affinity, the sequence is as follows: IgG1>IgG2c4a>IgG2m4>IgG2=IgGc4c>IgG2c4b>IgG4 ala/ala>IgG4 agly>IgG2c4d. This sequence is consistent in competition against IgG1 (CNT06234) in binding to FcgRIIb. Further competition binding analysis against IgG1 (CNT06234) in binding to FcRn at pH 6.4 indicated that all isotypes and mutants bind relatively equally to FcRn. Importantly, IgG2c4d and IgG1 agly show minimal, if any, detectable binding to FcgRIIa and FcgRIIb.

EXAMPLE 2

ADCC and CDC

CDC is initiated in three categories of pathway: antibody-dependent (classical pathway), polysaccharide dependent (lectin-dependent), and foreign surface structures (alternative pathway), all producing a cascade of proteolytic steps leading to the assembly of a membrane attack complex that culminates in target cell or microbial lysis (ref W. E. Paul Immunology). A subset of isotype and Fc mutants described in Example 1 were prepared using the variable domains of an anti-CD20 antibody and evaluated for their ability to lyse WIL2-S B-cell lymophoma target cells in the presence of human serum. Commercially available Rituxan®, a therapeutic anti-CD20 known to mediate CDC of WIL2-S cells was used a positive control for lysis. For CDC analysis, Wil2-S target cells were seeded in a 96-well plate, incubated with human serum complement (⅙ dilution) and relative cell viability was assessed using AlamarBlue.

The ADCC assay was performed using the anti-HER2/neu variable domain combined with the various Fc domains of the different IgG isotype or variants as described in Example 1 and SkBr3 breast cancer cells as targets. The assays were carried out as previously described using the EuTDA method of cell lysis detection (PerkinElmer, Waltham, Mass.). TDA-loaded SkBr3 breast cancer target cells were seeded in U-bottom 96-well plates, opsonized with designated concentrations of antibodies and co-cultured with 25× excess of PBMCs isolated from leukopacks at 37° C. After 3 hours, the plates were centrifuged, and supernatants were analyzed for TDA release according to manufacturer's instructions. Raw data was normalized and plotted using GraphPad Prism. For CDC analysis, Wil2-S target cells were seeded at 50,000 per well of a 96-well plate, incubated with human serum complement (⅙ dilution) and relative cell viability was assessed using AlamarBlue.

Results

Figure 4A:
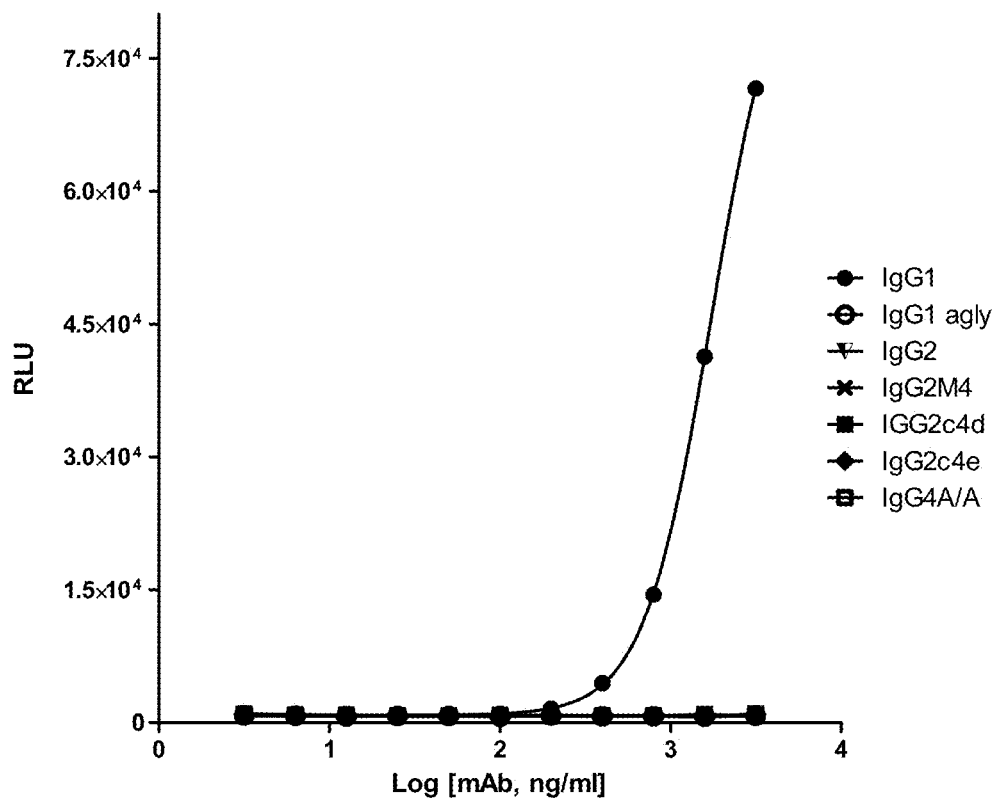
FIGS. 4A-C are graphs showing the direct binding of each isotype and mutant constructed as an anti-Her2/neu binding antibody using the AlphaScreen bead assay: FcgRIIIa (A), FcgRI (B), and FcgRIIa (C).
Figure 5:
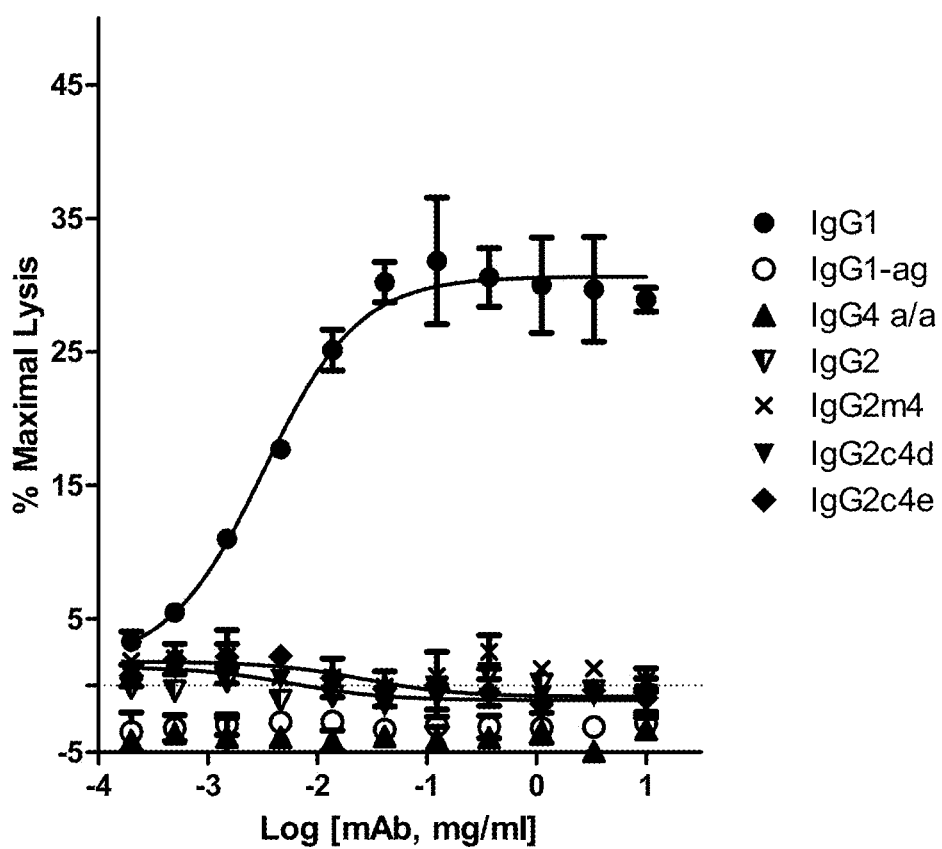
FIG. 5 shows the results of an ADCC assay and selected isotypes and mutants constructed as an anti-Her2/neu binding antibody and using human PBMCs (25× excess) and SK-Br3 breast cancer cells as targets.
Figure 6:
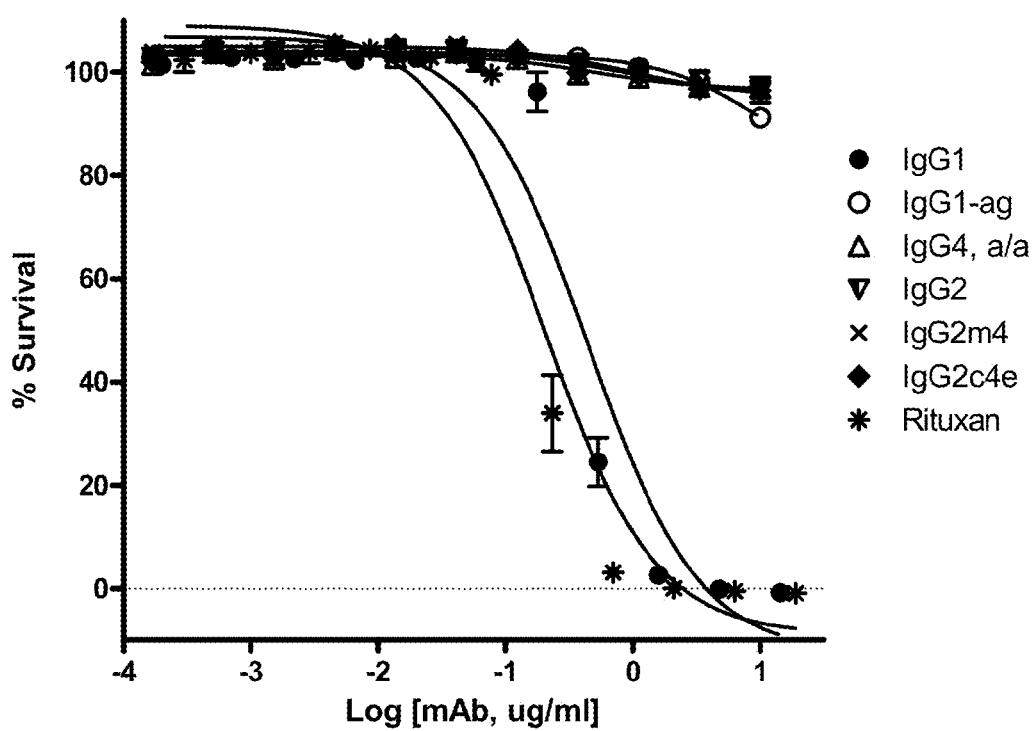
FIG. 6 shows the results of a CDC assay of selected anti-CD20 constructs using human complement and WIL2-S lymphoma cells as targets.

ADCC, which primarily engages FcgRIIIa on NK cells, was undetectable for the series of constructs tested which included IgG2, IgG2m4, IgG2c4d and e, IgG1 agly and IgG4 ala/ala (FIG. 5), consistent with the diminished binding characteristics shown for the higher affinity FcgRIIIa (V) receptor as well as the lack of avidity binding in the AlphaScreen™ assay (FIG. 4A). The use of high density targets, such as HER2/neu on breast cancer cells as in this study, demonstrated that Fc affinity for FcgRIIIa (lower than 40 uM) appears insufficient to induce target cell lysis. Similarly, none of the antibodies or Fc-mutants, aside from IgG1, demonstrated a significant level of CDC against WIL2-S target cells in the anti-CD20 constructs tested (FIG. 6). Among the IgG subclasses and mutants tested, only IgG1 demonstrated detectable levels of CDC, suggesting that independent of C1q binding, none of the remaining mutants can trigger CDC (FIG. 6). While previous efforts have pointed to IgG2 as having minimal CDC through C1q binding and activation of the classical pathway, we did not observe significant levels of activity in the anti-CD20 context, consistent with a previous observation (Idusogie, Presta et al. 2000 J Immunol 164(8): 4178-84). Moreover, previous indications of IgG1 agly having residual complement activity were also not detected using anti-CD20 and human serum (Dorai, Mueller et al. 1991 Hybridoma 10(2): 211-7). An explanation for this discrepancy is that while low levels of complement activation may be mediated by IgG2, activation may be insufficient to trigger the assembly of a membrane attack complexes (MAC) sufficient to lyse opsonized cells.

These data suggest that, regardless of the level of complement activation, the assembly of membrane attack complexes culminating in target cell lysis are deficient or insufficient for antibodies of isotypes other than bound IgG1.

EXAMPLE 3

Antibody-Dependent Cell Phagocytosis

The anti-HER2/neu binding Fc mutants were evaluated for their ability to mediate antibody-dependent cellular phagocytosis (ADCP), using opsonized target breast cancer cells, Sk-Br3 and macrophages.

Antibody-Dependent Cellular Phagocytosis (ADCP)

Peripheral blood mononuclear cells were isolated by standard Ficoll-Paque (GE Healthcare) density-gradient preparations from leukopacks (Biological Specialty Corporation), and cells were aliquoted and stored in nitrogen. PBMCs were thawed and CD14 positive cells were isolated by negative depletion using a CD14 Isolation kit without CD16 depletion (Stem Cell Technologies) per manufacturer instructions. Cells were plated at $0.1 \times 10^6$ cells/cm$^2$ in RPMI/ 5% heat-inactivated FBS/50 µg/ml gentimicin in the presence of 20 ng/ml GM-CSF (R&D Systems) for 7 days to generate monocyte-derived macrophages. SK-BR-3 tumor cells were labeled with PKH67 (Sigma) according to the manufacturer's instructions. Target cells were washed and incubated with monocyte-derived macrophages at a ratio of 1 target cell to 4 effector cells in the presence of antibodies for 4 hours at 37° C. in a 5% $CO_2$ incubator. After incubation, cells were detached with Accutase (Millipore), and macrophages were labeled with anti-CD11b antibodies (BD Biosciences) conjugated to AlexaFluor-647 (Invitrogen). Cells were analyzed by flow cytometry to determine tumor cells alone ($PKH67^{pos}$, $CD11b^{neg}$), macrophages alone ($PKH67^{neg}$, $CD11b^{pos}$), and phagocytosed tumor cells ($PKH67^{pos}$, $CD11b^{pos}$). Percent phagocytosis was determined by the following equation: (phagocytosed tumor cells)/(phagocytosed tumor cells plus tumor cells alone)× 100%. Cells were acquired on a FACS Calibur (Becton Dickinson), and the results were analyzed with FloJo Software (Tree Star).

Isolated monocytes were differentiated in vitro using GM-CSF and further characterized for the expression levels of FcRs by flow-cytometric analysis. As noted in previous studies by others, the GM-CSF activated macrophages expressed elevated levels of all FcRs (FcγRI, FcγRIIa, FcγRIIIa) relative to the parent monocytes (data not shown). The anti-HER2/neu IgG Fc mutant constructs were subsequently tested in phagocytosis assays using the M1 macrophages.

Results

Figure 4B:
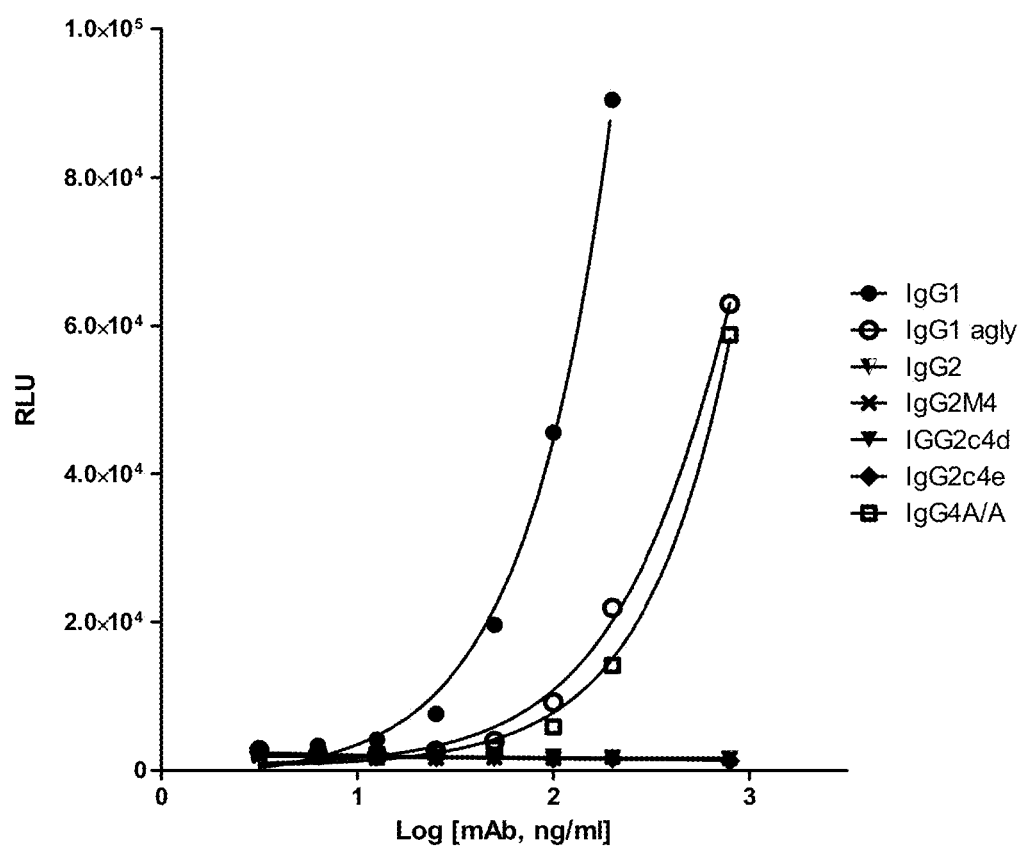
Figure 4C:
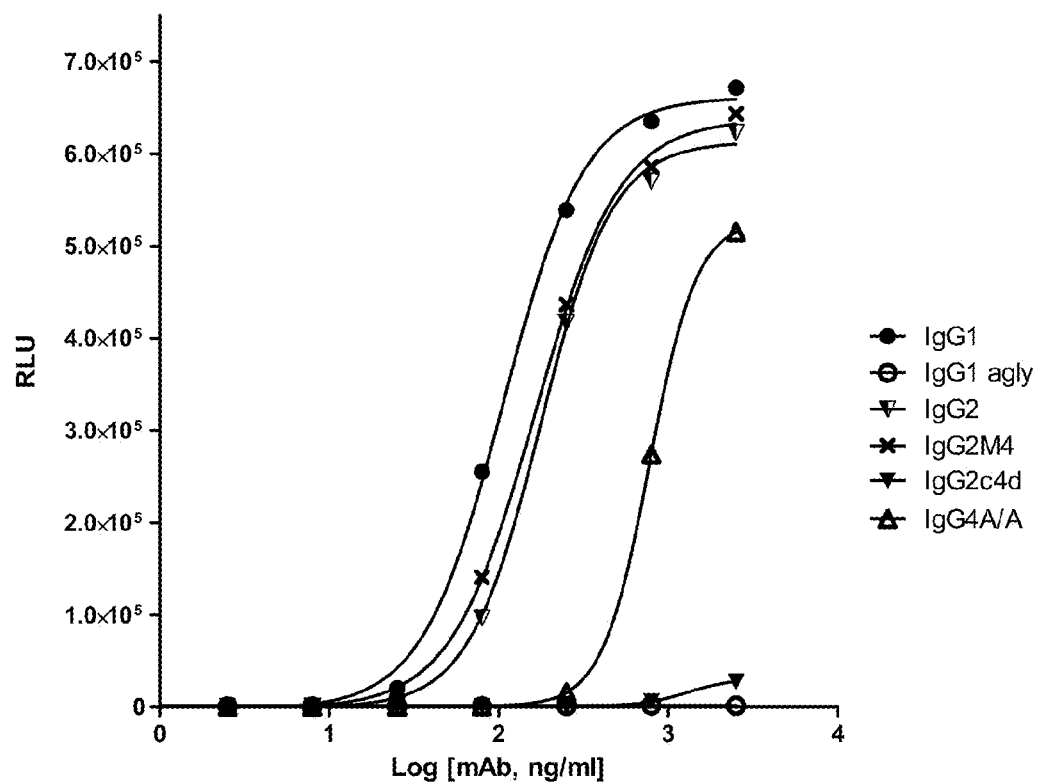
Figure 7:
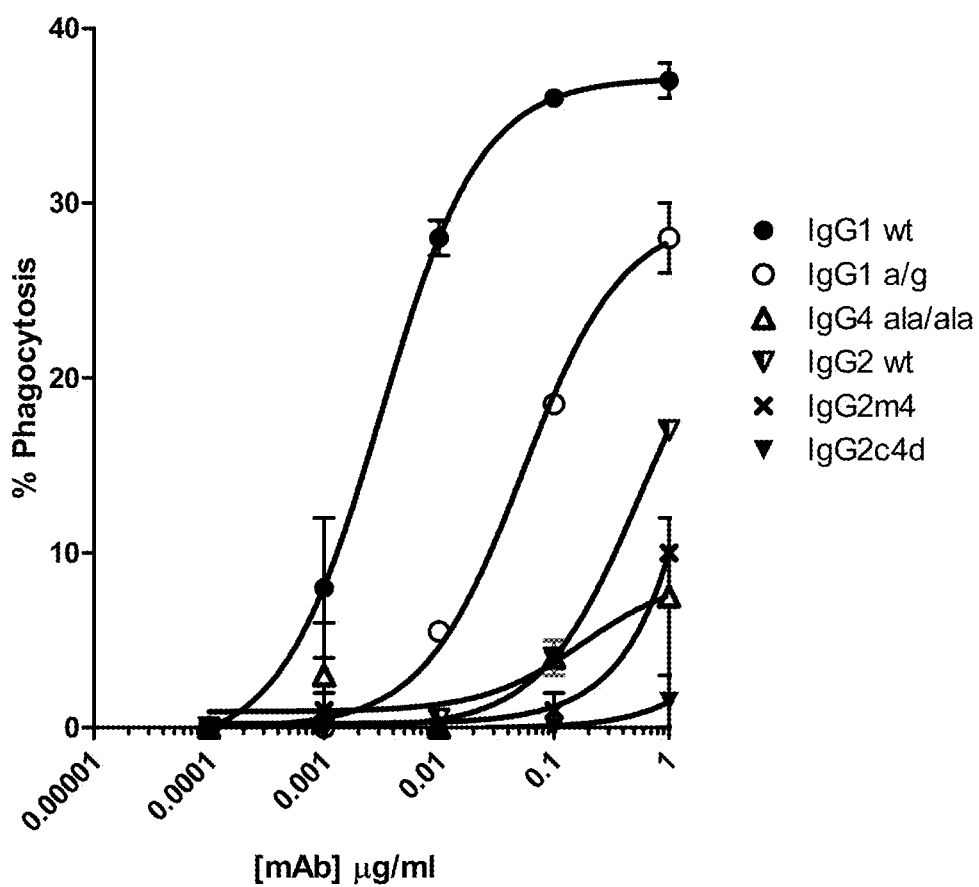
FIG. 7 shows the results of an ADCP assay from a flow cytometry analysis of selected anti-Her2/neu constructs using Sk-Br3 target cells and GM-CSF-differentiated macrophages.

After 4 hours of co-culture with SkBr3 cells in the presence of each mAb, significant levels of ADCP was apparent for IgG1, however minimal levels of ADCP were also observed for aglycosylated IgG1, IgG2, IgG2m4, and IgG4 S>P ala/ala at higher concentrations of antibody (FIG. 7). In contrast, IgG2c4d demonstrated no detectable levels of ADCP. This observation is consistent with the previously demonstrated binding profiles of the various IgGs against FcRs. For example, while IgG1, IgG agly and IgG4 ala/ala demonstrated binding in using the multiple ligand displaying beads (e.g using the AlphaScreen® system) to FcγRI, all three also demonstrated ADCP. IgG2 and IgG2M4 and IgG4 ala/ala showed minimal ADCP at higher concentrations. Engagement of FcγRIIa by IgG2 and IgG2m4, as shown by avidity studies suggests that the contribution of FcγRIIa may in and of itself be insufficient to drive significant levels of ADCP. The BiaCore and AlphaScreen™ results (Table 5 and FIGS. 4B and 4C) further indicated that while IgG agly has retained binding to FcγRI, IgG4 ala/ala shows avidity for both FcγRI and FcγRIIa, yet, ADCP is comparatively more robust for IgG1 agly than IgG4 ala/ala. Because IgG1 agly has minimal, if any, binding to FcγRIIa and by extension to the highly similar inhibitory FcγRIIb (based on sequence identity >95% in the extracellular doman) the activation of ITAMs through FcγRI signaling is not countered by signaling through ITIMs associated with FcγRIIb activation. In contrast, IgG4 S>P ala/ala shows a dampened phagocytosis, likely due to activation of FcγRIIb. Finally, the complete lack of detectable monomeric or avidity based binding of IgG2c4d to various FcRs further lends support to the unique abolished phagocytotic capacity of this Fc backbone.

EXAMPLE 4

Antibody-Mediated Cytokine Release

Fc-engagement of FcR on immune cells promotes cytokine release when cross-linked. In order to mimic the avidity-based engagement of FcRs on immune cells, mAbs were bound to polystyrene beads.

Cytokine release using anti-HER2/neu IgG mutants was performed after direct binding of IgGs to latex beads after overnight incubation. Washed beads were added to isolated human PBMCs at various concentrations as specified from about 1500 to 250,000 per ml and incubated overnight before removing co-culture supernatant to measure secreted TNFα using the standard AlphaELISA kit from PerkinElmer (Waltham, Mass.).

Figure 8:
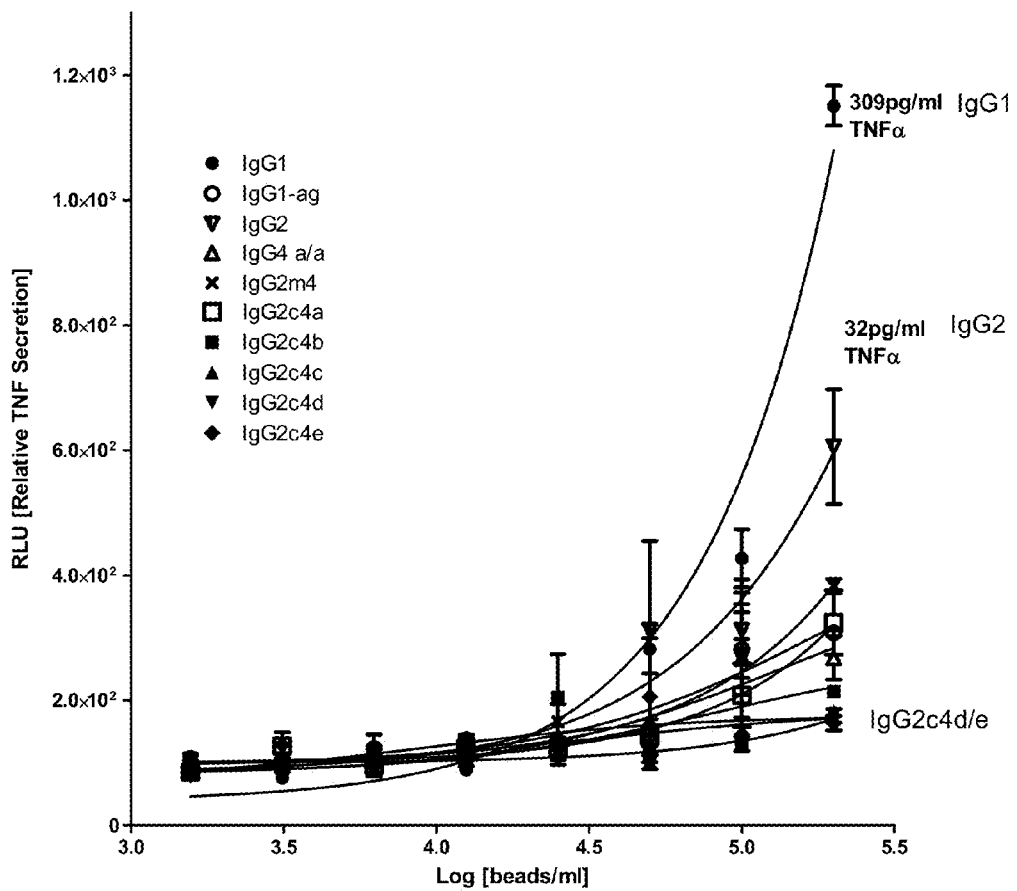
FIG. 8 is a graph showing the cytokine (TNFα) release from 24 hours after stimulation of PBMCs with beads bound to IgG isotypes for various constructs, including IgG2 wildtype and six mutants.

The tested IgG isotypes and Fc mutants possess differential ability to stimulate cytokine release through Fc receptor mediated TNFalpha secretion from PBMCs (FIG. 8). Accordingly, levels of TNF secretion by various isotypes and their Fc mutants from high to low, are as follows: IgG1>IgG2>IgG2m4>IgG2c4a>IgG1agly>IgG4ala/ ala>IgG2c4b>IgG2c4c>IgG4c4d and e. Of note, both IgG4d and e Fc mutants possess minimal, if any, capacity to induce detectable cytokine (TNF) release.

EXAMPLE 5

Ex vivo B Cell Depletion

To better understand the capacity of the isotypes and mutants in their level of silencing in vivo, ex vivo depletion of WIL2-S B-cells in the presence of heparinized whole human blood was determined. As an anti-CD20 IgG1 is known to engage all effector functions (ADCC, CDC, ADCP), the whole blood system, including the presence of PMNs (neutrophils, basophils, etc.), human complement, and excess IgG were considered to be representative of the level of 'silencing' conferred by each variant.

Briefly, whole human blood provided the effector cells and WIL2-S cells served as target cells for ADCC assays. Target cells were pre-labeled with BATDA (PerkinElmer) for 30 minutes at 37° C., washed twice and resuspended in DMEM/5% heat-inactivated FBS, then 50 µl of target ($2\times10^4$ cells per well) were added to the wells of 96-well U-bottom plates. An additional 50 µl was added with or without antibodies of various concentrations, and cells were incubated at room temperature for 20 minutes. Whole human blood (100 µl) was then added to the wells. All samples were performed in triplicate. The plates were centrifuged at 200 g for 3 minutes, incubated at 37° C. in a 5% $CO_2$ incubator for 3 hours, and then centrifuged again at 200 g for 3 minutes. A total of 20 µl of supernatant was removed per well and cell lysis was measured by the addition of 200 µl of the DELPHIA Europium-based reagent (PerkinElmer). Fluorescence was measured using an Envision 2101 Multi-label Reader (PerkinElmer). Data were normalized to maximal cytotoxicity obtained by treating cells with Triton X-100 (Sigma Aldrich) and minimal control determined by spontaneous release of BATDA from target cells alone. Data were fit to a sigmoidal dose-response model using GraphPad Prism v5.01.

Co-culturing of WIL2-S in the presence of human blood revealed severe effector-mediated depletion of labeled WIL2-S using IgG1 and to some extent by IgG2 and IgG2M4. Of note, (Fab')$_2$ and Fab anti-CD20 fragments both induced some level of WIL2-S depletion which may indicate the presence of a cleaved IgG autoantibody in the serum (see e.g. Breski et al. 2008 J Immunol 181:3183-3192) capable of restoring the effector function. Consistent with previous ADCC, CDC and ADCP data, no significant or detectable levels of cytokine release were observed with IgG2c4e.

EXAMPLE 6

In vivo B Cell Survival with CD20 Targeting

In vivo effector function associated with IgG2c4e was assessed using an established Cynomologous B-cell depletion model of anti-CD20 (Reff et al, 1994, Blood 83:435-445).

Figure 9:
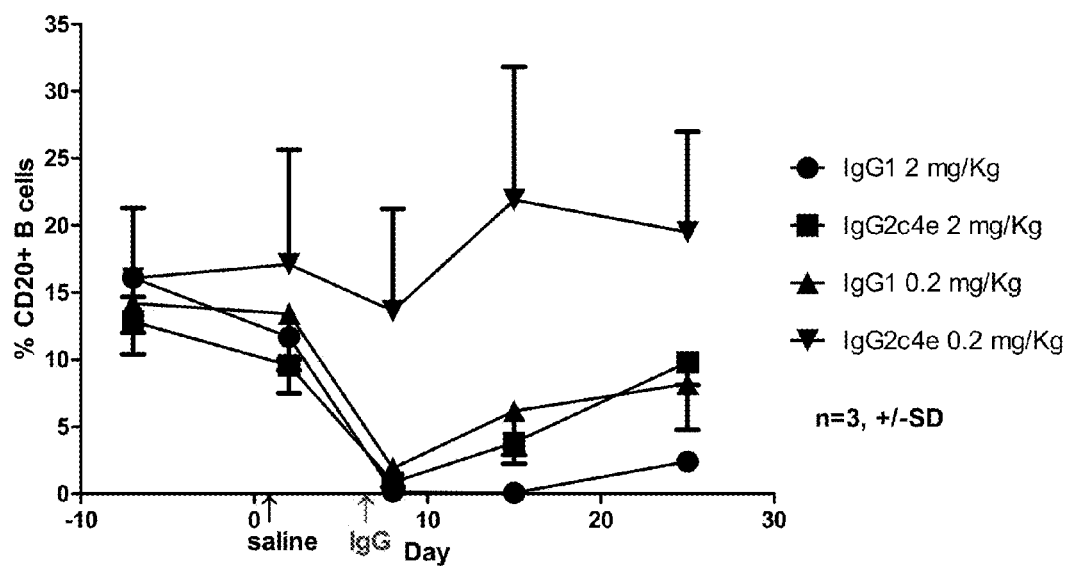
FIG. 9 is a graph of the mean circulating B-cell numbers over time in groups of cynomologous monkeys injected with anti-CD20 binding domain antibody constructs with various Fc regions or lacking an Fc-region (Fab')2.

Cynomologous monkeys (n=3/group) were injected with saline 7 days prior to single bolus intravenous doses of either IgG1 or IgG2Σ at 0.2 mg/Kg or 2 mg/Kg. On designated days following the injections, B cell levels from whole blood samples were determined by flow cytometry analysis of B and T cells using anti-CD20 and anti-CD3 as markers, respectively. The average B-cell levels (CD20+/CD3−) for each group were plotted during three weeks after injection (FIG. 9). While low doses of IgG1 (0.2 mg/kg) induced near complete depletion of all B-cells 1 day after injection (99%), no significant depletion was induced by anti-CD20 IgG2c4e (mean of 15% within the group). B cell levels remained relatively normal for the anti-CD20 IgG2c4e treated animals over the subsequent days, and there was a gradual trend toward recovery of B cell levels observed for IgG1 treated monkeys during subsequent weeks. Of note, both IgG2c4e and IgG1 induced near complete depletion of B-cells at the higher dose of 2 mg/Kg.

Anti-CD20 mediated B-cell depletion is thought to be mediated by several mechanisms, including ADCC, CDC and apoptosis. In view of the monkey B-cell depletion data indicating depletion of B-cells at the higher dose (2 mg/Kg) by IgG2c4e, the mechanistic basis of B-cell depletion was further evaluated by measuring levels of apoptosis induced by the antibodies in isolated B-cells.

Isolated B-cells were treated with 0, 0.26, 2.6 and 26 µg/ml concentrations of IgG1, IgG2c4e, (Fab')$_2$ and IgG2 as well as a non-binding control mAb (BM21) for 4 hrs and Annexin V positive, 7AAD negative cells were quantified by flow cytometry. Specific final concentrations of 2.6 and 26 µg/ml were selected to reflect estimated maximal in vivo concentrations of serum IgG after bolus injections of 0.2 and 2 mg/Kg.

For all three binding antibodies, a dose dependent induction of apoptosis was observed for all IgGs, including (Fab')$_2$, indicating that anti-CD20 mediated crosslinking is sufficient for induction of cell death at the higher dose, but not the lower dose for IgG2c4e. Of note, (Fab')$_2$ also demonstrated significant apoptosis in the absence of an Fc, confirming the notion that anti-IgG mediated apoptosis can be induced independent of Fc mediated cross-linking as previously observed.

Thus, the normal functions associated with cross-linking of target antigen on cells are not ablated by the modified Fc variant.

What is claimed:

1. A method of altering binding of an IgG2 based Fc-containing molecule to Fcγ receptors as compared to a wildtype IgG2 based Fc, comprising altering the sequence of an Fc domain based on an IgG2 constant region at residues 233, 234, 235, 237, and 238 defined by the EU numbering system, to comprise a sequence selected from PAAAS (SEQ ID NO:5) and SAAAS (SEQ ID NO:6), and altering the IgG2 based Fc-containing molecule to further comprise mutations H268A or H268Q, V309L, A330S and P331S, wherein the binding of the IgG2 based Fc-containing molecule to Fcγ receptors is reduced as compared to a wildtype IgG2 based Fc.

* * * * *

SEQUENCE LISTING

```
<160> NUMBER OF SEQ ID NOS: 6

<210> SEQ ID NO 1
<211> LENGTH: 226
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Hinge start, residue EU 218
<220> FEATURE:
<221> NAME/KEY: MUTAGEN
<222> LOCATION: (13)..(17)
<223> OTHER INFORMATION: PVAGP, PAAAP, PAAAS, and SAAAS
<220> FEATURE:
<221> NAME/KEY: MUTAGEN
<222> LOCATION: (47)..(47)
<223> OTHER INFORMATION: May be H (wt), Q, or A
<220> FEATURE:
<221> NAME/KEY: MUTAGEN
<222> LOCATION: (88)..(88)
```

```
<223> OTHER INFORMATION: May be V (wt) or L
<220> FEATURE:
<221> NAME/KEY: MUTAGEN
<222> LOCATION: (109)..(110)
<223> OTHER INFORMATION: May be AP (wt) or SS

<400> SEQUENCE: 1

Lys Cys Cys Val Glu Cys Pro Pro Cys Pro Ala Pro Xaa Xaa Ala Xaa
1               5                   10                  15

Xaa Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser Xaa Glu
        35                  40                  45

Asp Pro Glu Val Gln Phe Asn Trp Tyr Val Asp Gly Val Glu Val His
    50                  55                  60

Asn Ala Lys Thr Lys Pro Arg Glu Glu Gln Phe Asn Ser Thr Phe Arg
65                  70                  75                  80

Val Val Ser Val Leu Thr Val Xaa His Gln Asp Trp Leu Asn Gly Lys
                85                  90                  95

Glu Tyr Lys Cys Lys Val Ser Asn Lys Gly Leu Pro Xaa Xaa Ile Glu
            100                 105                 110

Lys Thr Ile Ser Lys Thr Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Met
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 2
<211> LENGTH: 227
<212> TYPE: PRT
<213> ORGANISM: Homo sapiens

<400> SEQUENCE: 2

Lys Tyr Gly Pro Pro Cys Pro Ser Cys Pro Ala Pro Glu Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser Gln
        35                  40                  45

Glu Asp Pro Glu Val Gln Phe Asn Trp Tyr Val Asp Gly Val Glu Val
    50                  55                  60

His Asn Ala Lys Thr Lys Pro Arg Glu Glu Gln Phe Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Gly Leu Pro Ser Ser Ile
                100                 105                 110

Glu Lys Thr Ile Ser Lys Ala Lys Gly Gln Pro Arg Glu Pro Gln Val
        115                 120                 125

Tyr Thr Leu Pro Pro Ser Gln Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Arg Leu Thr Val
            180                 185                 190

Asp Lys Ser Arg Trp Gln Glu Gly Asn Val Phe Ser Cys Ser Val Met
        195                 200                 205

His Glu Ala Leu His Asn His Tyr Thr Gln Lys Ser Leu Ser Leu Ser
    210                 215                 220

Leu Gly Lys
225

<210> SEQ ID NO 3
<211> LENGTH: 230
<212> TYPE: PRT
<213> ORGANISM: Homo sapiens

<400> SEQUENCE: 3

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
                100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
210                 215                 220

Ser Leu Ser Pro Gly Lys
225                 230
```

-continued

```
<210> SEQ ID NO 4
<211> LENGTH: 5
<212> TYPE: PRT
<213> ORGANISM: Artificial Sequence
<220> FEATURE:
<223> OTHER INFORMATION: human IgG residues and mutations

<400> SEQUENCE: 4

Pro Ala Ala Ala Pro
1               5

<210> SEQ ID NO 5
<211> LENGTH: 5
<212> TYPE: PRT
<213> ORGANISM: Artificial Sequence
<220> FEATURE:
<223> OTHER INFORMATION: human IgG residues and mutations

<400> SEQUENCE: 5

Pro Ala Ala Ala Ser
1               5

<210> SEQ ID NO 6
<211> LENGTH: 5
<212> TYPE: PRT
<213> ORGANISM: Artificial Sequence
<220> FEATURE:
<223> OTHER INFORMATION: human IgG residues and mutations

<400> SEQUENCE: 6

Ser Ala Ala Ala Ser
1               5
```